United States Patent [19]

Takematsu et al.

[11] 4,226,610
[45] Oct. 7, 1980

[54] HERBICIDAL COMPOUNDS, PREPARATION THEREOF AND HERBICIDES CONTAINING THE SAME

[75] Inventors: Tetsuo Takematsu; Makoto Konnai, both of Utsunomiya; Akira Suzuki, Tokyo; Kunitaka Tachibana, Yokohama; Takashi Tsuruoka, Kawasaki; Shigeharu Inouye; Tetsuro Watanabe, both of Yokohama, all of Japan

[73] Assignee: Meiji Seika Kaisha, Ltd., Tokyo, Japan

[21] Appl. No.: 27,900

[22] Filed: Apr. 6, 1979

[30] Foreign Application Priority Data

Apr. 15, 1978 [JP] Japan .................................. 53-44662
Jul. 4, 1978 [JP] Japan .................................. 53-80486

[51] Int. Cl.² .......................... A01N 57/00; C07F 9/02; C07C 103/52
[52] U.S. Cl. ................................. 71/86; 260/112.5 R; 260/502.5
[58] Field of Search .................. 260/112.5 R, 502.5; 71/86

[56] References Cited

U.S. PATENT DOCUMENTS

| | | | |
|---|---|---|---|
| 3,832,394 | 8/1974 | Nüda et al. | 260/112.5 R |
| 3,868,407 | 2/1975 | Franz et al. | 260/112.5 R |

OTHER PUBLICATIONS

Bayer, E., et al., "Chem. Abstracts", vol. 76, 83317b (1972).
Takematsu, Tetsuo, et al., "Chem. Abstracts", vol. 86, 12700s (1977).

*Primary Examiner*—Delbert R. Phillips
*Assistant Examiner*—Blondel Hazel
*Attorney, Agent, or Firm*—Frishauf, Holtz, Goodman & Woodward

[57] ABSTRACT

Novel compounds represented by formula (I) or (II) are provided:

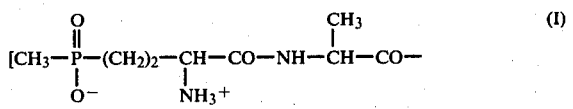

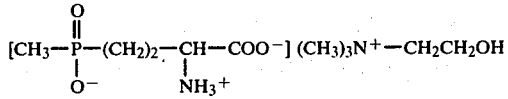

They can control annual and perennial weeds, shrubs and aquatic plants more effectively than their mother compounds, or (2-amino-4-methylphosphinobutyryl-)alanylalanine and 2-amino-4-methylphosphinobutanoic acid, respectively.

22 Claims, 3 Drawing Figures

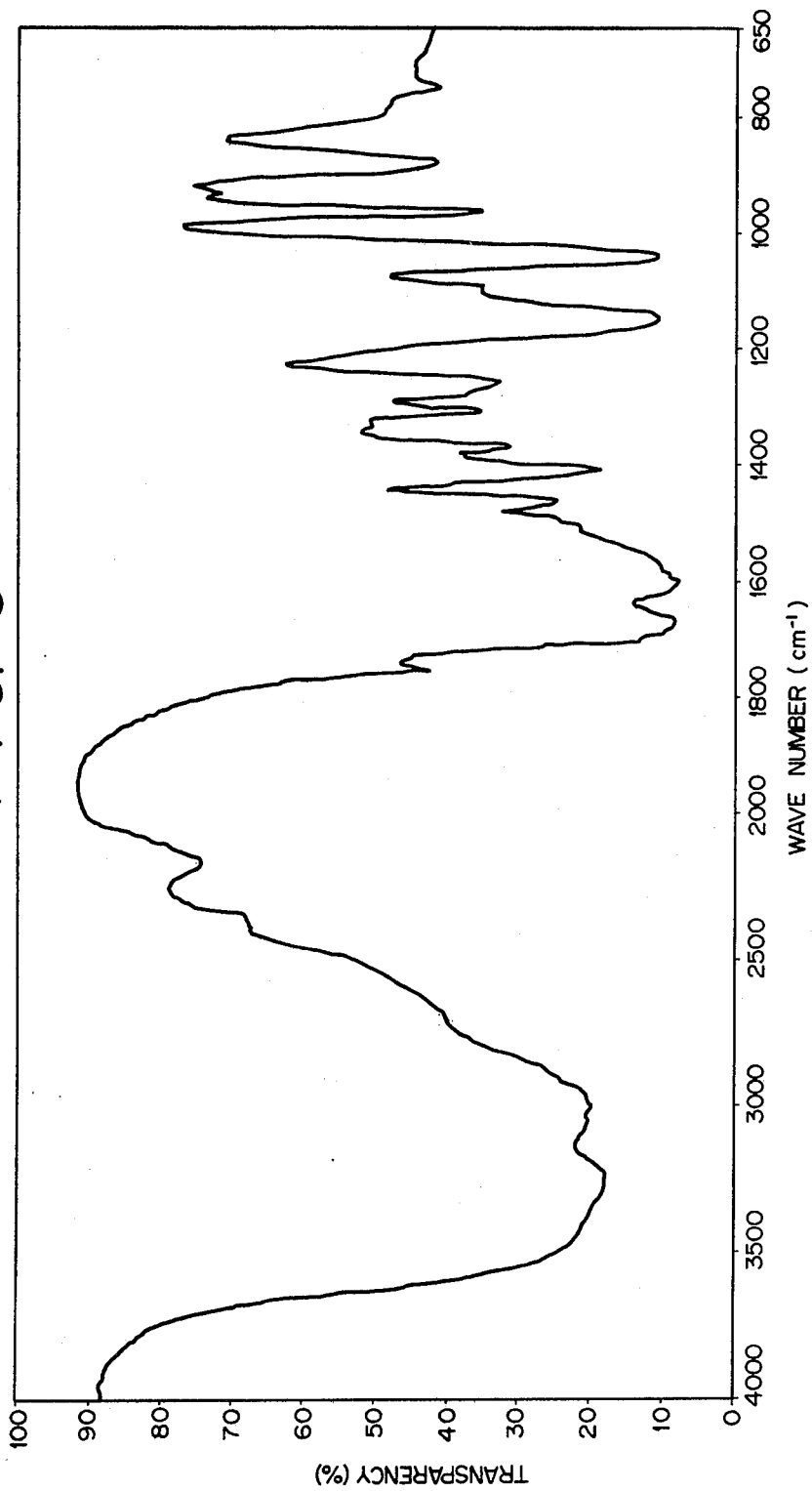

HERBICIDAL COMPOUNDS, PREPARATION THEREOF AND HERBICIDES CONTAINING THE SAME

The invention relates to novel herbicidal compounds, preparation thereof and herbicides containing the same.

More particularly, it relates to novel herbicidal compounds, or (2-amino-4-methylphosphinobutyryl)alanylalanine choline (hereinafter referred to as SF-1293 choline) and 2-amino-4-methylphosphinobutanoic acid choline (hereinafter referred to as AMPB choline) represented by formulae (I) or (II) preparation and herbicides containing the same:

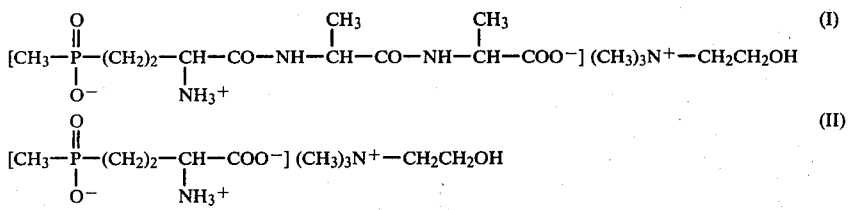

On the compounds represented by formula (III):

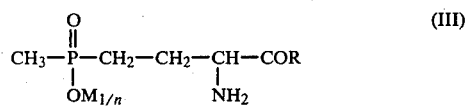

(wherein, R represents hydroxy group or alanylalanine residue; M represents hydrogen atom or a metal atom such as Na, K, Ca, Ba or Mg; n represents the valency of M), (2-amino-4-methylphosphinobutyryl)alanylalanine is known as a fermentation product of genus Streptomyces as disclosed in Japanese Patent Published Specification 48-22688/1973 as laid open to public inspection.

L-Form of 2-amino-4-methylphosphinobutanoic acid is known to be prepared by acidic hydrolysis of (2-amino-4-methylphosphinobutyryl)alanylalanine as disclosed in Japanese Patent Published Specification 48-85538/1973 as laid open to public inspection, or by enzymatic degradation thereof as disclosed in Japanese Patent Published Specification 49-31890/1974 as laid open to public inspection. DL-Form of 2-amino-4-methylphosphinobutanoic acid is known to be prepared by synthesis as disclosed in Japanese Patent Published Specification 48-91019/1973 as laid open to public inspection. The preparations were all developed by the present inventors.

It is known that the compounds represented by formula (III) are useful for herbicides as disclosed in Japanese Patent Application Specifications 52-133014/1977, 52-157421/1977, 52-154722/1977, 52-158932/1977 and 53-036059/1978.

The inventors have found, after studies of their derivatives in order to obtain more effective compounds, that the compounds represented by formulae (I) and (II) possess a stronger herbicidal effects than those of formula (III) and completed the invention.

It is, therefore, an object of the invention to provide novel compounds represented by formula (I) or (II).

It is another object of the invention to provide a process for preparing compounds of formula (I) or (II).

It is still another object of the invention to provide herbicidal compositions containing, as active ingredient, at least one compound represented by formula (I) or (II).

It is yet another object of the invention to provide a method of controlling upland and aqueous weeds by applying thereto at least one compound represented by formula (I) or (II).

DETAILED DESCRIPTION OF INVENTION

The compounds represented by formula (I) or (II) may be prepared by adding equimolar amount of cholines to aqueous solution of a compound of formula (III). Here, "cholines" mean choline and salts thereof with a mineral acid such as hydrochloric acid, sulfuric acid and phosphoric acid.

More specifically, the compounds of formula (I) or (II) may be prepared by adding equimolar amount of choline to aqueous solution of compound of formula (III) in which M represents hydrogen atom.

Alternatively, the compounds of formula (I) or (II) may be prepared by adding equimolar amount of choline salt with a mineral acid, such as hydrochloric acid, sulfuric acid and phosphoric acid, to aqueous solution of compound of formula (III) in which M represents Na, K, Ca, Ba, Mg or the like.

In the former case, it is preferable that decarbonated water is employed since choline tends to form a carbonate.

Thereafter, the above-mentioned aqueous solution is concentrated to dryness, the residue dissolved in 10 fold volume of a solvent such as methanol or ethanol. By adding 40 to 50 fold volume of an organic solvent such as ethyl acetate, chloroform, benzene or ether, there is obtained a white precipitate, which is dried in vacuo in the presence of a desiccant, giving the choline compound represented by formula (I) or (II) in the form of a white powder.

In the latter case, an inorganic salt is formed in the reaction solution as a by-product. The compound of formula (I) or (II) may be extracted from the concentrated residue of reaction solution with alcohol or a mixture thereof with acetone, if the inorganic salt is insoluble in water. If the inorganic salt is sparingly soluble in water, such as barium sulfate, it may be removed from the reaction solution by filtration for demineralization.

The compounds of formula (I) or (II) thus obtained have physicochemical properties shown in the following Table 1.

TABLE 1

| | | L-AMPB choline | DL-AMPB choline | SF-1293 choline |
|---|---|---|---|---|
| (1) | Appearance | white powder | white powder | white powder |

TABLE 1-continued

|     |                                  | L-AMPB choline                                      | DL-AMPB choline                                     | SF-1293 choline                                    |
| --- | -------------------------------- | --------------------------------------------------- | --------------------------------------------------- | -------------------------------------------------- |
| (2) | Melting Point                    | sintered at 135° C. melted at 175°–178° C.          | sintered at 105° C. melted at 152°–157° C.          | melted at 110°–112° C.                             |
| (3) | Molecular Formula                | $C_{10}H_{25}N_2O_5P$                               | $C_{10}H_{25}N_2O_5P$                               | $C_{16}H_{35}N_4O_7P$                              |
| (4) | Elementary Analysis (%)          | C,42.20; H,8.83 N,9.81; P,10.98                     | C,42.18; H,8.82 N,9.79; P,10.97                     | C,45.02; H,8.23 N,13.10; P,7.33                    |
| (5) | Specific Rotatory Powder         | $[\alpha]_D^{20} -13.8°$ (C = 1, methanol)          | $[\alpha]_D^{23} 0.0°$ (C = 1, methanol)            | $[\alpha]_D^{22} -1.2°$ (C = 1, methanol)          |
| (6) | UV Ray Absorption                | terminal absorption                                 | terminal absorption                                 | terminal absorption                                |
| (7) | IR Ray Absorption                | shown in FIG. 1                                     | shown in FIG. 2                                     | shown in FIG. 3                                    |
| (8) | Mass-spectrometry m/e            | 285 (M + 1)                                         | 285 (M + 1)                                         |                                                    |
| (9) | Solubility (mg/ml)               | 95 (ethanol)                                        | 164 (ethanol)                                       | 310 (ethanol)                                      |
| (10)| Cellulose Thin Layer ($R_f$) Chromatog. | 0.31                                         | 0.31                                                | 0.58                                               |

The substances prepared by the above-mentioned treatments were confirmed to be unitary compounds represented by formula (I) or (II) by mass-spectrometric and thin-layer chromatographic analyses. Namely, AMPB choline gives a protonated molecular ion peak $(M+1)^+$ at m/e 285 by field desorption masschromatometry, suggesting that AMPB choline is a unitary compound. Further, AMPB choline gives a single spot at $R_f 0.31$ by cellulose thin-layer chromatography (developping solvent: ethanol/water=4:1) when detected with both ninhydrin and Dragendorff reagents, suggesting that AMPB is a unitary compound. Here, AMPB and AMPB-containing substances show bluish violet color reaction with ninhydrin reagent, while no AMPB-containing substances do not. Similarly, choline and choline-containing substances show reddish brown color reaction with Dragendorff reagent, while AMPB does not.

Although the compounds of the invention absorb moisture incidentally upon prolonged storage, they may be served for stable herbicides by formulating them into liquid formulation, dust formulation, fine granules, wettable powder or the like as mentioned in the following description.

In recent years, the growth of perennial weeds has been a problem not only in non-crop land but also in paddy field, upland, orchard and meadow. The basis of perenial weeds are in their underground part, namely rhizome, tuber, bulb and root. They store nutrients a lot and show a strong reproductive germination. A complete control of perennial weeds may not be attained merely by killing the uppergound parts due to emergence of new bodies from the underground parts. It may be attained by inhibiting the reproduction.

Therefore, perennial weeds have far strong resistance to herbicides than annual weeds. In cropland, they propagate with their clonal propagation organs at the underground parts finely divided and distributed by cultivation, agitation and movement of soil. Heretofore, N-phosphonomethylglycine (hereinafter referred to as glyphosate) is known as the controlling agent for perennial weeds; but it has an disadvantage that it is not so effective for broad-leaved weeds. Therefore, there have been desired herbicides having a broad weeding spectrum with excellent effects. If has been also a serious problem to control shrubs in non-crop land, meadow and afforested land. For instance, in afforested land, large perennial weeds such as miyakozasa (*Sasa nipponica* Makino et Shibata) and eulalia (*Miscanthus sinensis* Andress.) and shrubs such as kumaichigo (*Rubus crataegifolius* Bunge), chestnut (*Castanea crenata* Sieb or Zucc.) and Japanese bush cranberry (*Viburnum dilatatum* Thunb.) predominate over Japanese cedar (*Cryptomeria japonica* D. Don) and Japanese cypress (*Chamaecyparis obtusa* Endl.) in competition for nutrients, water and light. Also in meadow, the control of shrubs around there is a problem. There are few herbicides effective for shrubs because of difficulty in controlling it. Namely, unlike herbaceous plants, shrubs have a hard bark to prevent, the penetration of controlling agents; they have a developed reproduction mechanism or branches even after defoliation; and they are generally larger than herbaceous plants.

The compounds of the invention show quite excellent weeding effects by foliar or soil treatments. Particularly, if they are subjected to foliar application to annual and perennial weeds and shrubs, they show not only strong contact effects but also translocate in plants and kill the growth point, thus exhibiting the following superior properties.

To wit, they kill annual grass having strong reproducing ability such as manna grass (*Digitaria adscendens* Henr.) and cockspar grass (*Echinochloa Crus-galli* P. Beauv.) and inhibit their reproduction. When they are subjected to foliar application to perennial weeds, they translocate to underground parts such as rhizome, tuber, bulb, corm or root, which are the basis of life of perennial weeds, and kill the underground parts. As the results, perennial weeds are controlled by foliar application, preventing the reproduction of underground parts which is most difficult but important in perennial weeds control.

There are few herbicides known to control shrubs effectively. When the compounds of the invention are subjected to foliar application, they translocate to every part, exhibiting strong killing effects and reproduction-inhibiting effects. The reproduction-inhibiting effects for weeds and shrubs by the compounds of the invention are superior to those of glyphosate in the following points. Namely, the compounds of the invention are more effective than glyphosate at lower concentration.

While glyphosate has poor weeding effects for broad-leaved weeds and shrubs, the compounds of the invention show quite strong activities to almost all of weeds and shrubs, except for Japanese cypress, and have an extremely broad weeding spectrum.

When weeding activities of AMPB choline and SF-1293 choline are compared with those of monosodium salt of 2-amino-4-methylphosphinobutanoic acid or monodiethanolammonium salt of 2-amino-4-methylphosphinobutanoic acid, and monosodium salt of (L-2-amino-4-methylphosphinobutyryl)-L-alanyl-L-alanine or monodiethylammonium salt of (L-2-amino-4-methylphosphinobutyryl)-L-alanyl-L-alanine, respectively, the compounds of the invention are superior to the prior art herbicides with respect to both killing effects of upperground parts and reproduction-inhibiting effects. Particularly, their differences may be observed in the reproduction-inhibiting effects, as shown in the following Experiments. L-AMPB choline is, for instance, twice effective than monosodium or monodiethylammonium salts of L-2-amino-4-methylphosphinobutanoic acid, as shown in Experiment 1.

Another problem in controlling weeds is that the period when weeds flourish, i.e. the period when the weed control is most required coincides with the rainy season. It is usually difficult in the rainy season to spray herbicides by watching the time when the weather is fine. The herbicides sprayed tend to be flown down with rain which begins to fall immediately after the spray.

one of the characteristics of the compounds of the invention is that they may readily be absorbed and penetrated into plants after foliar application and are not influenced by rainfall. In other words, the compounds of the invention have quite and excellent resistance to rain. This characteristic make the compounds of the invention advantageous under conditions when the metabolism of plants is in low level and absorption and penetration of herbicides are inhibited, or when they are sprayed at low temperature or at later stage of growth of plants in autumn treatment.

As mentioned above, the compounds of the invention have strong weeding effects for almost all of annual and perennial weeds and shrubs, except for Japanese cypress, and therefore, may be used alone for controlling of all sorts of weeds and shrubs. Further, they may inhibit the reproduction and recovery or weeds and shrubs strongly, and therefore, possess quite a high practical value.

The development of afforested land and bottom weed control therein are quite a heavy work. Accordingly, recent decrease in workers engaged in the work has been a problem.

The compounds of the invention fit for the development of afforested land since, as previously described, they have strong weeding effects for large perennial weeds and shrubs. As they have no phytotoxicity to Japanese cypress, they may be used for selective herbicides in Japanese cypress afforested land to control bottom weeds.

The compounds of the invention may readily be formulated into dust formulation and fine granules which are commonly used in afforested land. This is because it is difficult to obtain water in afforested land and the formulations may cause no phytotoxicity to needle-leaved trees such as Japanese cedar due to small adhesion. It is, therefore, to be understood that the compounds of the invention may be used not only in Japanese cypress afforested land but also in e.g. Japanese cedar afforested land for bottom weed control, by formulating them into such formulations.

There are few herbicides effective for both weeds and shrubs. For example, while sodium 2,2,3,3-tetrafluoropropionate is an afforested land herbicide effective for eulalia and bamboo grass, it is not so effective for shrubs. Accordingly, shrubs such as kumaichigo, chestnut and Japanese bush cranberry begin to grow after the control of eulalia and bamboo grass. As the result, it becomes necessary to employ a herbicide to control the growth of shrubs.

The compounds of the invention, on the contrary, may kill both weeds and shrubs strongly and inhibit the reproduction and recovery for a long period. The compounds of the invention, therefore, may be said to be epoch making herbicides.

While the compounds of the invention may retain the effects in plants over a long period, they may comparatively rapidly be inactivated in soil. Accordingly, they can control weeds in upland over a long period when they are applied before sowing, without any phytotoxicity to sowed plants. When they are used in paddy field by autumn treatment after harvesting for controlling of perennial weeds or the like, they translocate to plants and inhibit the reproduction from the underground parts in the next spring.

As they are comparatively rapidly inactivated in soil, adsorbed on the surface of soil, they may also be applied in orchard. Namely, if they are used in orchard for bottom weed control, they cause no phytotoxicity to plants because they are not absorbed from roots of plants.

The compounds of the invention may also be applied in various places, besides afforested land and crop land.

For instance, in meadow, shrubs often grow around there. Further, weeds such as bitter dock (*Rumex obtusifolius* L.) grow in competition with pastures. It is anticipated from this that they quality of milk may be lowered if cows eat weeds. Furthermore, weeds bearing prickles such as warunasubi (*Solanum carolinense* L.) may become cause of injury for cattles. The compounds of the invention may kill weeds and shrubs among pastures by way of spot treatment.

Further, the compounds of the invention may be used for controlling of annual and perennial weeds and shrubs in factory, railroad, park, public facility, riverbed, bank, high way, golf link, rested crop land and new broken land.

The amound of the compounds of the invention needed for killing of weeds and shrubs, and inhibiting of reproduction thereof may vary, depending on climatic conditions such as temperature and light intensity as well as species of weeds and shrubs to be treated.

The amount of active ingredients will be illustrated in the following Table 2.

TABLE 2

| Example of weeds and shrubs | DL-AMPB choline | | L-AMPB choline | | SF-1293 choline | |
|---|---|---|---|---|---|---|
| | Dust Formul. | Liquid Formul. | Dust Formul. | Liquid Formul. | Dust Formul. | Liquid Formul. |
| Annual weeds and perennial weeds of less than 1 m in height such as wormweed, curly dock and purple | 25 to 2000 | 25 to 1000 | 10 to 1000 | 10 to 500 | 25 to 1600 | 25 to 800 |

TABLE 2-continued

| | DL-AMPB choline | | L-AMPB choline | | SF-1293 choline | |
|---|---|---|---|---|---|---|
| Example of weeds and shrubs | Dust Formul. | Liquid Formul. | Dust Formul. | Liquid Formul. | Dust Formul. | Liquid Formul. |
| nutsedge Perennial weeds of more than 1 m in height such as miyakozasa and eulalia and small shrubs such as torch azalea and kumaichigo | 75 to 3200 | 75 to 1600 | 35 to 1600 | 35 to 800 | 75 to 2000 | 75 to 1000 |
| Large shrubs such as chestnut and oak and inhibition of new buds from large stumps | 150 to 6400 | 150 to 3200 | 75 to 3200 | 75 to 1600 | 150 to 4000 | 150 to 2000 |

Remark:
In the Table, the amount of herbicide to be applied is indicated by gram per 10 are.

The compounds of the invention may control effectively not only upland and lowland plants but also algae and higher aquatic plants. Here "higher aquatic plants" means aquatic plants which are taxonomically higher than algae.

They include, for example, plants which are submerged wholly in water and extend the roots under the bottom of the water, those a part of which are emerged from the surface of water, and those which are floating on or in water. The aquatic plants bring about various disadvantages to our life as mentioned below. For example, if weeds flourish in waterway, the flow rate in rivers of water decreases as compared with the original plan. This causes sedimentation of soil and sand, change in water temperature, increase of erosion of waterway, interruption of river transportation and decrease in number of fish.

It is also known that aquatic plants floating and increasing on the surface of water, such as water hyacinth (*Eichhornia crassipes Solms* Laub.), brings about serious problems on the functions of water supply and drainage in canal, lake and swamp, dam, and irrigation water. In fact, water hyacinth is an serious harmful weed in waterway mainly in tropical and subtropical zones.

Further, the growth of aquatic plants may make swimming and fishing in lake and swamp impossible and restrict severely the utility of water for industrial and sight-seeing purposes.

The compounds of the invention may kill every sort of aquatic plants, including water hyacinth which is a worldwidely harmful perennial weed in waterway, and inhibit reproduction thereof without any toxicity of fish. The excellent herbicidal activity of the compounds of the invention ascribes to the superior penetration and absorption on the surface of plants and translocation in plants after penetration. In case of perennial weeds such as water hyacinth, the compounds of the invention inhibit the reproduction of new leaves from the base completely, leading to the death.

The inventors have further found that the compounds of the invention may effectively control wide varieties of submerged weeds if they are dissolved into still water at a determined concentration, by inhibiting the reproduction of weeds. Furthermore, the compounds of the invention may control algae such as pond scums (*Spirogyra*) and diatoms (Diatomacae).

The greatest advantage of the compounds of the invention when applied to aquatic plants is that they have quite a low toxicity to fish ($LC_{50} > 20$ ppm) and show an excellent selectivity between fish and weeds and algae for which the control is required. The fact makes the compounds of the invention valuable for the practical use as herbicide for aquatic plants.

When the compounds of the invention are applied foliarly to aquatic plants floating on the surface of water, or growing on the surface of water and extending the roots under the bottom of water, they are diluted in water and give no toxicity to fish at all.

Further, if the compounds of the invention are formulated into a flowable formulation as disclosed in Japanese Patent Published Specification 41-10037/1965 entitled "Water surface-spreading insecticidal compositions", they form a thin layer around the surface of water for some period and are absorbed acceleratedly by weeds growing around the surface of water, and at the same time, are not taken into fish. Thus, the enhancement of effects and prevention of fish toxicity may be attained at the same time.

The amount of compounds of the invention need for controlling of aquatic plants will vary depending on various conditions. In case of foliar application, aquatic weeds and algae may be controlled by spraying a solution containing 0.01 to 1.0% of active ingredient in an amount of 25 to 250 liter per 10 are. In case of submerged application, aquatic plants and algae may be killed by maintaining the concentration of active ingredient in still water at 0.1 to 20 ppm.

For controlling of upland and lowland weeds and shrubs, and aquatic plants and algae, the compounds of the invention may be formulated into various forms, with appropriate diluents, such as liquid formulation, water-soluble formulation, wettable powder, emulsifiable concentrate, dust formulation, fine granules or the like. The formulations may contain surfactants such as octylphenyl polyoxyethanol, polyoxyethylene dodecyl ether, polyoxyethylene sorbitan fatty acid ester, polyoxyethylene alkylaryl ether or the like in order to improve spreading, adhesive or dispersing properties and make sure of or enhance the effects.

The formulations may further contain other herbicides such as germination-inhibiting agents and foliar applicating agents so as to enhance the effects of the compounds of the invention and prolonging the controllable period thereof.

BRIEF DESCRIPTION OF THE DRAWINGS

FIG. 3 shows infrared spectrum of product obtained in Preparation 3, or (L-2-amino-4-methylphosphinobutyryl)-L-alanyl-L-alanine choline.

DESCRIPTION OF THE PREFERRED EMBODIMENT

Figure 1:
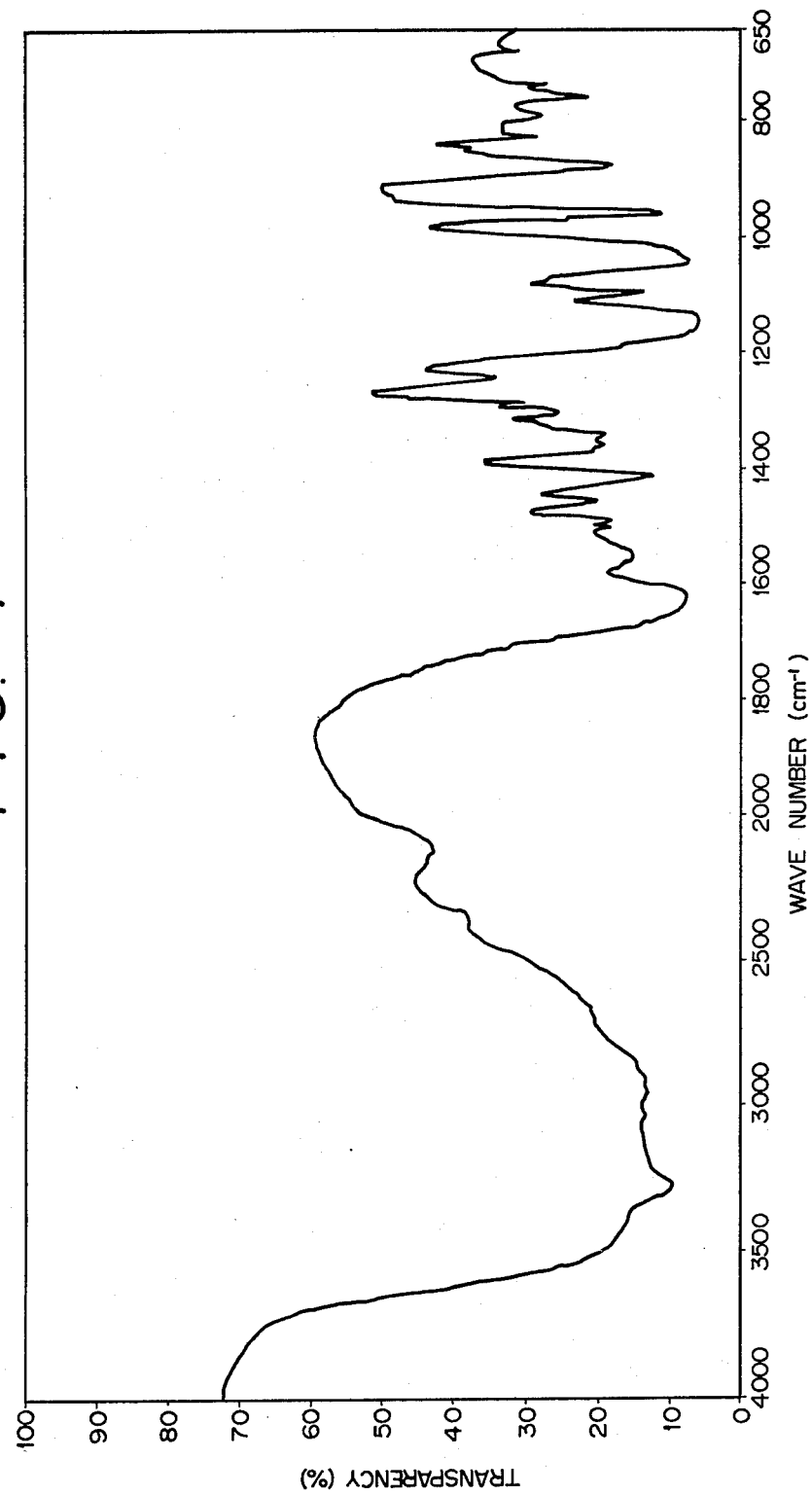
FIG. 1 shows infrared spectrum of product obtained in Preparation 1, or L-2-amino-4-methylphosphinobutanoic acid choline.

The invention is further explained by the following Preparations, Formulations and Experiment which do not, by any means, restrict the scope of the invention. The percent and part are by weight in hereinafter description, unless otherwise defined.

Preparation 1. L-2-Amino-4-methylphosphino-butanoic acid choline 3.55 g. of L-2-amino-4-methylphosphinobutanoic acid was dissolved in 50 ml. of boiled and cooled water, and 2.38 g. of choline was added thereto. The mixture was concentrated and the resulting residue was dissolved in 50 ml. of ethanol. A white precipitate was separated out by adding 50 ml. of ethyl acetate. The supernatant was discarded by decantation and the precipitate was washed with a small amount of ethyl acetate and dried in vacuo over phosphorus pentoxide, giving 5.4 g. of L-2-amino-4-methylphosphinobutanoic acid choline in the form of a white powder.

Melting point; 175°–178° C.

Elementary analysis (%) for $C_{10}H_{25}N_2O_5P$; Calcd. C, 42.25; H, 8.86; N, 9.85; P, 10.90. Found C, 42.20; H, 8.83; N, 9.81; P, 10.98. IR Spectrum; as shown in FIG. 7.

Preparation 2, DL-2-Amino-4-methylphosphinobutanoic acid choline 2.49 g. of barium salt of DL-2-amino-4-methylphosphinobutanoic acid was dissolved in 25 ml. of water and 1.52 g. of choline sulfate was added thereto.

The precipitate of resulting barium sulfate was filtered off and the filtrate was condensed. The residue was dissolved in 25 ml. of ethanol and a white precipitate was separated out by adding 250 ml. of acetone. The supernatant was discarded by decantation and the precipitate was washed with a small amount of acetone and dried in vacuo over phosphorus pentoxide, affording 2.75 g. of DL-2-amino-4-methylphosphinobutanoic acid choline in the form of a white powder.

Melting point; 152°–157° C.

Figure 2:
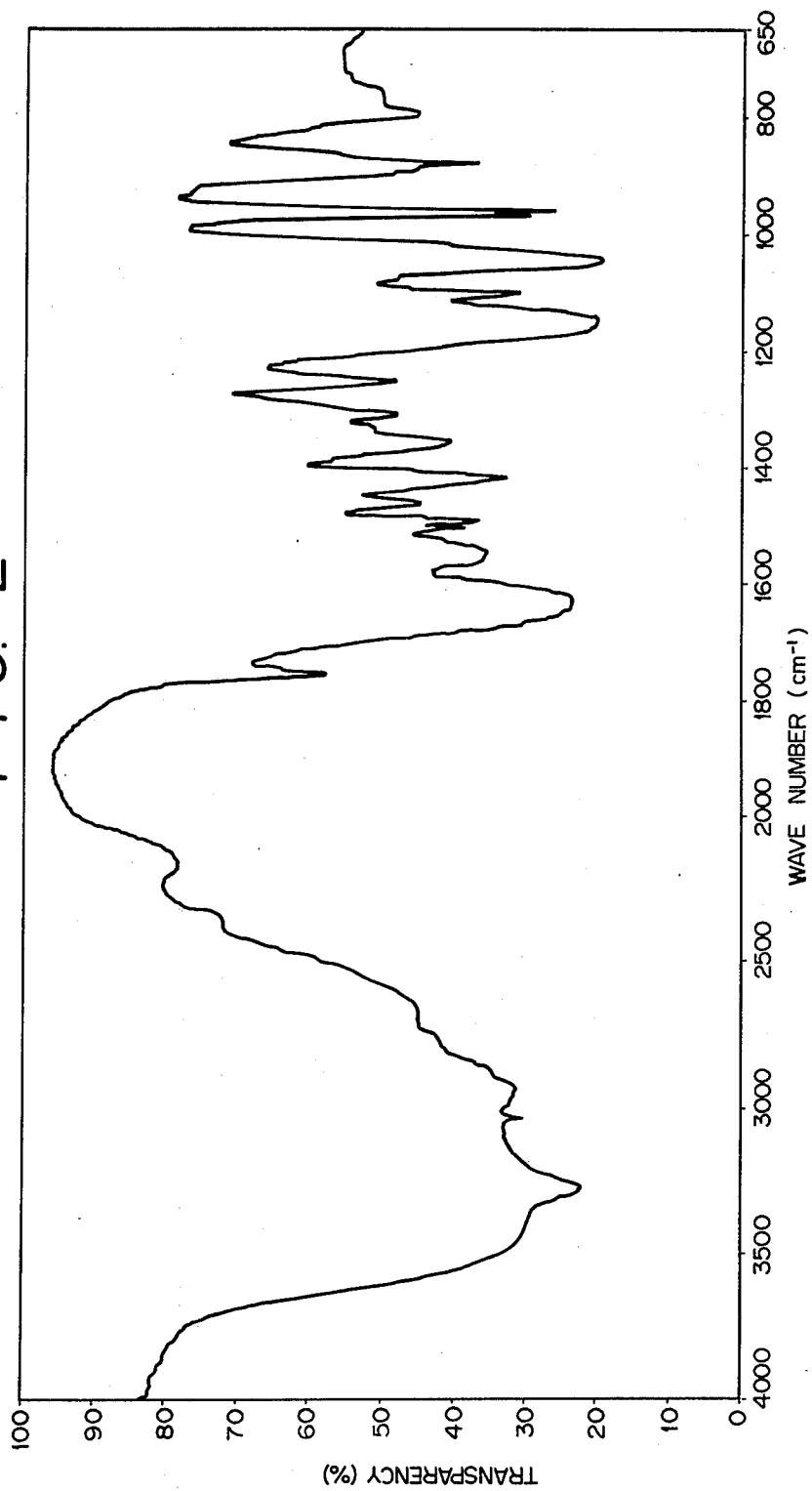
FIG. 2 shows infrared spectrum of product obtained in Preparation 2, or DL-2-amino-4-methylphosphinobutanoic acid choline.

Elementary analysis (%) for $C_{10}H_{25}N_2O_5P$; Calc. C, 42.25; H, 8.86; N, 9.85; P, 10.90. Found C, 42.18; H, 8.82; N, 9.79; P, 10.97. IR Spectrum; as shown in FIG. 2.

Preparation 3. (L-2-Amino-4-methylphosphinobutyryl)-L-alanyl-L-alanine choline 3.23 g. of (L-2-amino-4-methylphosphinobutyryl)-L-alanyl-L-alanine was dissolved in 25 ml. of boiled and cooled water and 1.21 g. of choline was added thereto. The mixture was concentrated and the residue was dissolved in 25 ml of methanol.

A white precipitate was separated out by adding 50 ml. of ether. The supernatant was discarded by decantation and the precipitate was washed with a small amount of ether and dried over phosphorus pentoxide, yielding 4.26 g. of (L-2-amino-4-methylphosphinobutyryl)-L-alanyl-L-alanine choline in the form of a white powder.

Melting point; 110° C.

Elementary analysis (%) for $C_{16}H_{35}N_4O_7P$; Calc. C, 45.07; H, 8.27; N, 13.14; P, 7.26. Found C, 45.02; H, 8.23; N, 13.10; P, 7.33. IR Spectruml as shown in FIG. 3.

Formulation 1. Dust Formulation 4.0% of L-AMPB choline, 95.0% of talc and 1.0% of fine powder of anhydrous silicic acid were pulverized and blended to make a dust formulation. Upon application to upland and lowland weeds and shrubs, it is subjected to foliar application as such.

Formulation 2. Liquid Formulation 30.0% of SF-1293 choline, 15.0% of octylphenyl polyoxyethanol, 0.15% of methyl p-hydroxybenzoate and 54.85% of water were dissolved and mixed to make a liquid formulation. Upon application to upland and lowland weeds and shrubs, it is diluted with water and subjected to foliar application.

Formulation 3. Wettable Powder 45.0% of DL-AMPB choline, 50.0% of diatomaceous earth and 5.0% of nonionic/anionic surfactant were pulverized, blended homogeneously and finely to make a wettable powder. Upon application to upland and lowland weeds and shrubs, it is diluted with water and subjected to foliar application.

Formulation 4. Liquid Formulation 30.0% of DL-AMPB choline, 15.0% of octylphenyl polyoxyethanol, 0.15% of methyl p-hydroxybenzoate and 54.85% of water were dissolved and mixed to make liquid formulation. Upon application to aquatic plants, it is diluted with water and subjected to foliar or submerged application.

Formulation 5. Wettable Powder 50.0% of L-AMPB choline, 45.0% of diatomaceous earth and 5.0% of nonionic/anionic surfactant were pulverized and blended homogeneously, finely to make a wettable powder.

Upon application to aquatic plants, it is diluted with water and subjected to foliar or submerged application.

Formulation 6. Dust Formulation

5% of SF-1293 choline and 95% of talc were pulverized and blended homogeneously to make a dust formulation. Upon application to aquatic plants, it is subjected as such to foliar application in an amount of 0.4–6 kg. per 10 are.

The following are Experiments of the invention.

The detail of the assessment made in the following Experiments of the invention was as follows:

| Killing Index | Foliage Damage (%) |
|---|---|
| 0 | O |
| 1 | 20% |
| 2 | 40% |
| 3 | 60% |
| 4 | 80% |
| 5 | 100% |

Four months after treatment, evaluation was made for inhibition of reproduction expressed in terms of symbols ranging from (−) to (+++) where (−) means no reproduction, namely complete suppression of reproduction, (±) remarkable suppression of reproduction; (+) considerable suppression of reproduction; (++)

medium suppression of reproduction; and (+++) no suppression of reproduction.

EXPERIMENT 1

The compounds of the invention and other compounds for comparison listed in Table 3 were diluted to prescribed concentrations and sprayed to naturally growing weeds by foliar application in an amount of 150 liter per 10 are.

0.1% of octylphenyl polyoxyethanol was added as a surfactant.

The killing index (0, no effect, 5, death) after 21 days, and the reproduction-inhibiting effect (−, no reproduction; +++, maximum reproduction) after 2 months (manna grass and cockspar grass) and 4 months (other weeds) were determined.

The results are shown in Table 3.

TABLE 3

| Compound and the concentration (%) | | Killing index of Upperground parts | | | | | | | | | Reproduction - inhibiting effect | | | | | | | | |
|---|---|---|---|---|---|---|---|---|---|---|---|---|---|---|---|---|---|---|
| | | A | B | C | D | E | F | G | H | I | A | B | C | D | E | F | G | H | I |
| L-2-Amino-4-methyl-phosphino-butanoic acid monosodium salt | 0.05 | 3 | 3 | 3 | 1 | 3 | 3 | 3 | 2.5 | 3 | ++ | ++ | ++ | +++ | +++ | +++ | +++ | ++ | ++ |
| | 0.1 | 4.5 | 4.5 | 5 | 3 | 5 | 5 | 4.5 | 4.5 | 5 | ± | ± | + | + | + | ++ | + | − | − |
| | 0.2 | 5 | 5 | 5 | 5 | 5 | 5 | 5 | 5 | 5 | − | − | ± | ± | ± | + | − | − | − |
| DL-2-Amino-4-methyl-phosphino-butanoic acid monosodium salt | 0.05 | 1 | 1 | 1 | 0 | 2 | 2 | 1 | 1 | 2 | +++ | +++ | +++ | +++ | +++ | +++ | +++ | +++ | ++ |
| | 0.1 | 3 | 3 | 3 | 1 | 4 | 5 | 3 | 3 | 4 | ++ | ++ | +++ | +++ | +++ | +++ | +++ | + | ++ |
| | 0.2 | 4.5 | 4.5 | 5 | 3 | 5 | 5 | 4.5 | 5 | 5 | ± | ± | ++ | + | + | +++ | + | − | − |
| (L-2-Amino-4-methyl-phosophino-butyryl)—L-Alanyl—L-alanine monosodium salt | 0.05 | 1 | 1 | 3 | 1 | 3 | 3 | 1.5 | 2 | 4 | +++ | +++ | +++ | +++ | +++ | +++ | +++ | +++ | |
| | 0.1 | 3 | 3 | 4 | 2 | 4 | 5 | 3.5 | 4 | 5 | ++ | ++ | ++ | +++ | +++ | +++ | +++ | + | ++ |
| | 0.2 | 4 | 4 | 5 | 3 | 5 | 5 | 5 | 5 | 5 | ± | ± | ± | + | + | +++ | + | − | − |
| L-2-Amino-4-methyl-phosphino-butanoic acid mono diethanol-ammonium salt | 0.05 | 3 | 3 | 3 | 1 | 3 | 3 | 3 | 3 | 3 | ++ | ++ | ++ | +++ | +++ | +++ | +++ | ++ | ++ |
| | 0.1 | 5 | 5 | 5 | 3 | 5 | 5 | 5 | 5 | 5 | − | − | + | + | + | ++ | − | − | − |
| | 0.2 | 5 | 5 | 5 | 5 | 5 | 5 | 5 | 5 | 5 | − | − | ± | ± | ± | + | − | − | − |
| DL-2-Amino-4-methyl-phosphino-butanoic acid mono diethanol-ammonium salt | 0.05 | 1 | 1 | 1 | 0 | 2 | 2 | 1 | 1 | 2.5 | +++ | +++ | +++ | +++ | +++ | +++ | +++ | +++ | +++ |
| | 0.1 | 3 | 3 | 3 | 1 | 4 | 4 | 3 | 3 | 4 | ++ | ++ | +++ | +++ | +++ | +++ | +++ | + | ++ |
| | 0.2 | 5 | 5 | 5 | 3 | 5 | 5 | 5 | 5 | 5 | − | − | ++ | + | + | +++ | − | − | − |
| (L-2-Amino-4-methyl-phosphino butylryl)—L-alanyl—L-alanine mono-diethanol-ammoniom salt | 0.05 | 1 | 1 | 3 | 1 | 3 | 3 | 2 | 2 | 4 | +++ | +++ | +++ | +++ | +++ | +++ | +++ | +++ | +++ |
| | 0.1 | 3.5 | 3.5 | 4 | 2 | 4 | 5 | 4 | 4 | 5 | ++ | ++ | ++ | +++ | +++ | +++ | +++ | + | ++ |
| | 0.2 | 4.5 | 4.5 | 5 | 4 | 5 | 5 | 5 | 5 | 5 | − | − | ± | + | + | +++ | − | − | − |
| L-AMPB choline | 0.05 | 4 | 4 | 4 | 3 | 4 | 4 | 4 | 3 | 4 | ± | ± | ± | + | ± | ± | ± | ± | − |
| | 0.1 | 5 | 5 | 5 | 4 | 5 | 5 | 5 | 5 | 5 | − | − | − | ± | − | − | − | − | − |
| | 0.2 | 5 | 5 | 5 | 5 | 5 | 5 | 5 | 5 | 5 | − | − | − | − | − | − | − | − | − |
| DL-AMPB choline | 0.05 | 2 | 2 | 2 | 1 | 3 | 3 | 1.5 | 1.5 | 3 | ++ | ++ | ++ | ++ | ++ | ++ | ++ | ++ | ++ |
| | 0.1 | 4 | 4 | 4 | 2 | 4.5 | 5 | 4 | 3.5 | 4.5 | ± | ± | ± | + | ± | ± | ± | ± | − |
| | 0.2 | 5 | 5 | 5 | 4 | 5 | 5 | 5 | 5 | 5 | − | − | − | ± | − | − | − | − | − |
| SF-1293 choline | 0.05 | 2 | 2 | 3.5 | 2 | 3.5 | 4 | 3 | 3 | 4 | + | + | ++ | ++ | ++ | + | + | + | + |
| | 0.1 | 4.5 | 4.5 | 5 | 3 | 5 | 5 | 5 | 5 | 5 | ± | ± | ± | + | ± | ± | − | − | − |
| | 0.2 | 5 | 5 | 5 | 5 | 5 | 5 | 5 | 5 | 5 | − | − | − | ± | − | − | − | − | − |
| Glypho-sate | 0.05 | 1 | 1 | 0 | 0 | 1 | 1 | 1 | 0 | 0 | +++ | +++ | +++ | +++ | +++ | +++ | +++ | +++ | +++ |
| | 0.1 | 3 | 3 | 1 | 2 | 3 | 2 | 2 | 1 | 1 | ++ | ++ | +++ | +++ | +++ | +++ | ++ | ++ | ++ |
| | 0.2 | 5 | 5 | 2 | 4 | 4 | 4 | 3 | 4 | 4 | + | + | ++ | + | + | +++ | + | + | ± |

TABLE 3-continued

| Compound and the concentration (%) | Killing index of Upperground parts | | | | | | | | | Reproduction - inhibiting effect | | | | | | | | |
|---|---|---|---|---|---|---|---|---|---|---|---|---|---|---|---|---|---|---|
| | A | B | C | D | E | F | G | H | I | A | B | C | D | E | F | G | H | I |
| None | 0 | 0 | 0 | 0 | 0 | 0 | 0 | 0 | 0 | +++ | +++ | +++ | +++ | +++ | +++ | +++ | +++ | +++ |

Remarks:
A: manna grass (*Digitaria adsceudes* Henr.)
B: cockspar grass (*Echinochloa Crus-galli* P. Beauv.)
C: yabugarashi (*Cayratia japonica* Houtt.)
D: purple nutsedge (*Cyperus rotundus* L.)
E: warunasubi (*Solanum carolinensis* L.)
F: hedge bindweed (*Calystegis hederacea* Wall.)
G: white clover (*Trifolium repens* L.)
H: azumanezasa (*Pleioblastus Chino* Makino)
I: chigaya (*Imperata cylindrica* Beauv.)

EXPERIMENT 2

The compounds of the invention and other compounds listed in Table 4. were diluted to prescribed concentrations and sprayed to shrubs by foliar application in a Japanese cypress afforested land in an amount of 150 liter per 10 are.

After 30 days and 3 months, the killing index (0, no effect; 5, death) was determined.

The heights of plants were 50–70 cm. for Japanese cypress, about 50 cm. for chestnut, 50–90 cm. for miyakozasa, about 100 cm. for eulalia and 70–100 cm. for kumaichigo, respectively.

The results are shown in Table 4.

TABLE 4

| Compound and the concentration (%) | | After 30 days | | | | | After 3 months | | | | |
|---|---|---|---|---|---|---|---|---|---|---|---|
| | | J | K | L | M | N | J | K | L | M | N |
| L-2-Amino-4-methylphosphino-butanoic acid monosodium salt | 0.063 | 0 | 2 | 2 | 1 | 3 | 0 | 1 | 0 | 0 | 2 |
| | 0.125 | 0 | 5 | 4 | 3.5 | 4.5 | 0 | 5 | 5 | 4.5 | 5 |
| | 0.25 | 0 | 5 | 5 | 5 | 5 | 0 | 5 | 5 | 5 | 5 |
| DL-2-Amino-4-methylphosphino-butanoic acid monosodium salt | 0.063 | 0 | 0.5 | 0 | 0 | 1.5 | 0 | 0 | 0 | 0 | 0 |
| | 0.125 | 0 | 2 | 2 | 2.5 | 3 | 0 | 1 | 1 | 1 | 1 |
| | 0.25 | 0 | 5 | 4 | 4 | 4 | 0 | 5 | 5 | 5 | 5 |
| (L-2-Amino-4-methyl-phosphinobutyryl)—L-alanyl—L-alanine monosodium salt | 0.063 | 0 | 1 | 1 | 1 | 1 | 0 | 0 | 0 | 0 | 0 |
| | 0.125 | 0 | 4 | 3 | 3 | 4 | 0 | 3 | 2 | 2 | 3 |
| | 0.25 | 0 | 5 | 4 | 4 | 4.5 | 0 | 5 | 4 | 4 | 5 |
| L-2-Amino-4-methylphosphino-butanoic acid mono-diethanolammonium salt | 0.063 | 0 | 2 | 2 | 1 | 3 | 0 | 1 | 1 | 1 | 2 |
| | 0.125 | 0 | 5 | 5 | 3.5 | 4.5 | 0 | 5 | 5 | 5 | 5 |
| | 0.25 | 0 | 5 | 5 | 5 | 5 | 0 | 5 | 5 | 5 | 5 |
| DL-2-Amino-4-methylphosphino-butanoic acid monodiethanol-ammonium salt | 0.063 | 0 | 1 | 0 | 0 | 2 | 0 | 0 | 0 | 0 | 0 |
| | 0.125 | 0 | 2 | 2 | 3 | 3 | 0 | 1 | 1 | 1.5 | 1.5 |
| | 0.25 | 0 | 5 | 5 | 4 | 4 | 0 | 5 | 5 | 5 | 5 |
| (L-2-Amino-4-methyl-phosphinobutyryl)—L-alanyl—L-alanine monodiethanol-ammonium salt | 0.063 | 0 | 1 | 1 | 1 | 1 | 0 | 0 | 0 | 0 | 0 |
| | 0.125 | 0 | 4 | 3 | 3 | 4 | 0 | 3 | 2 | 2 | 3 |
| | 0.25 | 0 | 5 | 4.5 | 4.5 | 5 | 0 | 5 | 4.5 | 4.5 | 5 |
| L-AMPB choline | 0.063 | 0 | 3.5 | 3 | 3 | 4 | 0 | 5 | 4 | 3.5 | 5 |
| " | 0.125 | 0 | 5 | 5 | 4 | 5 | 0 | 5 | 5 | 5 | 5 |
| " | 0.25 | 0 | 5 | 5 | 5 | 5 | 0 | 5 | 5 | 5 | 5 |
| DL-AMPB choline | 0.063 | 0 | 2 | 1 | 1 | 2 | 0 | 1 | 0 | 0 | 1 |
| " | 0.125 | 0 | 4 | 3 | 4 | 4 | 0 | 5 | 3 | 4.5 | 5 |
| " | 0.25 | 0 | 5 | 5 | 5 | 5 | 0 | 5 | 5 | 5 | 5 |
| SF-1293 choline | 0.063 | 0 | 3 | 2 | 2 | 3 | 0 | 2 | 1 | 1 | 2 |
| " | 0.125 | 0 | 5 | 4 | 4 | 5 | 0 | 5 | 4.5 | 4.5 | 5 |
| " | 0.25 | 0 | 5 | 5 | 5 | 5 | 0 | 5 | 5 | 5 | 5 |
| Glyphosate | 0.063 | 0 | 0 | 0 | 0 | 0 | 0 | 0 | 0 | 0 | 0 |
| " | 0.125 | 2 | 2 | 2 | 2 | 1 | 2 | 1 | 2 | 2 | 0.5 |
| " | 0.25 | 3 | 3 | 4 | 4 | 2 | 3 | 2 | 3 | 3 | 1 |
| 2,2,3,3-Tetra-fluoropropionic acid sodium salt | 0.125 | 0 | 0 | 1 | 1 | 0 | 0 | 0 | 0 | 0 | 0 |
| | 0.25 | 0 | 0 | 3 | 3 | 0 | 0 | 0 | 1 | 1 | 0 |
| | 0.5 | 0 | 0 | 4 | 4.5 | 0 | 0 | 0 | 4 | 4 | 0 |
| None | | 0 | 0 | 0 | 0 | 0 | 0 | 0 | 0 | 0 | 0 |

Remarks:
J: Japanese cypress (*Chamaecyparis obtusa* Endle.)
K: chestnut (*Castanea crenata* Sieb et Zucc.)
L: miyakozasa (*Sasa nipponica* Makino et Shibata)
M: eulalia (*Miscanthus sinensis* Andress.)
N: kumaichigo (*Rubus crataegifolius* Bunge)

EXPERIMENT 3

The compounds of the invention and other compounds listed in Table 5. were diluted to prescribed concentrations and sprayed onto naturally growing shrubs by foliar application in an amount of 150 liter per 10 are.

0.1% of octylphenyl polyoxyethanol was added as the surfactant. The killing index (0, no effect; 5, death) after 1 month and 3 months, and the reproduction-inhibiting effect (−, no reproduction; +++, maximum reproduction) after 3 months were determined.

The results are shown in Table 5.

TABLE 5

| Compound and the concentration (%) | | Killing index | | | | | | | | | | | | |
|---|---|---|---|---|---|---|---|---|---|---|---|---|---|---|
| | | After 30 days | | | | | | After 3 months | | | | | | |
| | | O | P | Q | R | S | T | U | O | P | Q | R | S | T | U |
| L-2-Amino-4-methylphosphino-butanoic acid monosodium salt | 0.05 | 2 | 3.5 | 4 | 3.5 | 3 | 3 | 3 | 1 | 1.5 | 1 | 2 | 1.5 | 1 | 1 |
| | 0.1 | 4 | 5 | 5 | 5 | 4 | 5 | 5 | 3 | 5 | 4 | 5 | 5 | 5 | 5 |
| | 0.2 | 5 | 5 | 5 | 5 | 5 | 5 | 5 | 4 | 5 | 5 | 5 | 5 | 5 | 5 |
| DL-2-Amino-4-methylphosphino-butanoic acid monosodium salt | 0.05 | 0 | 1 | 1 | 1 | 1 | 1 | 1 | 0 | 0 | 0 | 0 | 0 | 0 | 0 |
| | 0.1 | 1 | 3 | 3 | 3 | 3 | 3 | 3 | 1 | 1 | 1 | 1 | 1 | 1 | 1 |
| | 0.2 | 3 | 5 | 5 | 5 | 4 | 5 | 5 | 2 | 5 | 5 | 5 | 5 | 5 | 5 |
| (L-2-Amino-4-methylphosphino-butyryl)-L-alanyl-L-alanine monosodium salt | 0.05 | 2 | 3 | 2 | 1 | 1 | 1 | 1 | 1 | 1 | 1 | 0 | 0 | 0 | 0 |
| | 0.1 | 4 | 5 | 4 | 3 | 3 | 3 | 3 | 3 | 3 | 3 | 1 | 1 | 1 | 1 |
| | 0.2 | 5 | 5 | 5 | 5 | 4 | 5 | 5 | 5 | 5 | 5 | 5 | 5 | 5 | 5 |
| L-2-Amino-4-methylphosphino-butanoic acid monodiethanol-ammonium salt | 0.05 | 2 | 3.5 | 4 | 3.5 | 3 | 3 | 3 | 1 | 2 | 1 | 2 | 2 | 1 | 1 |
| | 0.1 | 4.5 | 5 | 5 | 5 | 5 | 5 | 5 | 3 | 5 | 4.5 | 5 | 5 | 5 | 5 |
| | 0.2 | 5 | 5 | 5 | 5 | 5 | 5 | 5 | 4 | 5 | 5 | 5 | 5 | 5 | 5 |
| DL-2-Amino-4-methylphosphino-butanoic acid monodiethanol-ammonium salt | 0.05 | 0 | 1 | 1 | 1 | 1 | 1 | 1 | 0 | 0 | 0 | 0 | 0 | 0 | 0 |
| | 0.1 | 1 | 4 | 3 | 3 | 3 | 4 | 3 | 1 | 2 | 1 | 1 | 1 | 2 | 1 |
| | 0.2 | 3 | 5 | 5 | 5 | 4 | 5 | 5 | 2 | 5 | 5 | 5 | 5 | 5 | 5 |
| (L-2-Amino-4-butyryl)-L-alanyl-L-alanine mono-diethanolam-monium salt | 0.05 | 2 | 3 | 2 | 1 | 1 | 1 | 1 | 1 | 1 | 1 | 0 | 0 | 0 | 0 |
| | 0.1 | 4 | 5 | 4 | 3 | 3 | 4 | 3 | 3 | 3 | 3 | 1 | 1 | 2 | 1 |
| | 0.2 | 5 | 5 | 5 | 5 | 4 | 5 | 5 | 5 | 5 | 5 | 5 | 5 | 5 | 5 |
| L-AMPB choline | 0.05 | 3 | 4.5 | 4.5 | 4.5 | 4 | 4 | 4 | 4 | 5 | 4.5 | 4.5 | 5 | 5 | 5 |
| | 0.1 | 5 | 5 | 5 | 5 | 5 | 5 | 5 | 5 | 5 | 5 | 5 | 5 | 5 | 5 |
| | 0.2 | 5 | 5 | 5 | 5 | 5 | 5 | 5 | 5 | 5 | 5 | 5 | 5 | 5 | 5 |
| DL-AMPB choline | 0.05 | 1 | 2 | 2 | 2 | 2 | 2 | 2 | 1 | 3 | 1 | 1 | 1 | 1 | 1 |
| | 0.1 | 3 | 4 | 4 | 4 | 4 | 5 | 4 | 2 | 4.5 | 3 | 5 | 5 | 5 | 5 |
| | 0.2 | 4 | 5 | 5 | 5 | 5 | 5 | 5 | 4 | 5 | 5 | 5 | 5 | 5 | 5 |
| SF-1293 choline | 0.05 | 3 | 4 | 3 | 2 | 2 | 2 | 2 | 2 | 2 | 2 | 1 | 1 | 1 | 1 |
| | 0.1 | 5 | 5 | 5 | 4 | 4 | 4.5 | 4 | 5 | 5 | 4.5 | 5 | 5 | 5 | 5 |
| | 0.2 | 5 | 5 | 5 | 5 | 5 | 5 | 5 | 5 | 5 | 5 | 5 | 5 | 5 | 5 |
| Glyphosate | 0.05 | 0 | 0 | 0 | 0 | 0 | 0 | 0 | 0 | 0 | 0 | 0 | 0 | 0 | 0 |
| | 0.1 | 0 | 1 | 0 | 0 | 1 | 1 | 1 | 0 | 0 | 0 | 0 | 0 | 0 | 0 |
| | 0.2 | 1.5 | 2 | 0 | 1 | 2 | 2 | 2 | 1 | 1 | 0 | 0 | 1 | 0 | 0 |
| 2,2,3,3-Tetra-fluoro propionic acid sodium salt | 0.1 | 0 | 0 | 0 | 0 | 0 | 0 | 0 | 0 | 0 | 0 | 0 | 0 | 0 | 0 |
| | 0.2 | 0 | 0 | 0 | 0 | 0 | 0 | 0 | 0 | 0 | 0 | 0 | 0 | 0 | 0 |
| | 0.4 | 0 | 0 | 0 | 0 | 0 | 0 | 0 | 0 | 0 | 0 | 0 | 0 | 0 | 0 |
| None | 0 | 0 | 0 | 0 | 0 | 0 | 0 | 0 | 0 | 0 | 0 | 0 | 0 | 0 | 0 |

| Compound and the concentration (%) | | Reproduction-inhibiting after 3 months | | | | | | |
|---|---|---|---|---|---|---|---|---|
| | | O | P | Q | R | S | T | U |
| L-2-Amino-4-methylphosphino-butanoic acid monosodium salt | 0.05 | +++ | ++ | +++++ | | ++ | +++ | ++ |
| | 0.1 | ++ | − | + | − | − | − | − |
| | 0.2 | − | − | − | − | − | − | − |
| DL-2-Amino-4-methylphosphino-butanoic acid monosodium salt | 0.05 | +++ | +++ | ++++++ | | +++ | +++ | +++ |
| | 0.1 | ++ | ++ | ++ | ++ | ++ | ++ | ++ |
| | 0.2 | ++ | − | − | − | − | − | − |
| (L-2-Amino-4-methylphosphino-butyryl)-L-alanyl-L-alanine monosodium salt | 0.05 | +++ | +++ | ++++++ | | +++ | +++ | +++ |
| | 0.1 | + | + | + | ++ | ++ | ++ | ++ |
| | 0.2 | − | − | − | − | − | − | − |
| L-2-Amino-4-methylphosphino-butanoic acid monodiethanol-ammonium salt | 0.05 | +++ | ++ | +++++ | | ++ | +++ | ++ |
| | 0.1 | ++ | − | ± | − | − | − | − |
| | 0.2 | − | − | − | − | − | − | − |
| DL-2-Amino-4-methylphosphino-butanoic acid monodiethanol-ammonium salt | 0.05 | +++ | +++ | ++++++ | | +++ | +++ | +++ |
| | 0.1 | ++ | ++ | ++ | ++ | ++ | ++ | ++ |
| | 0.2 | ++ | − | − | − | − | − | − |

TABLE 5-continued

| | | | | | | | | |
|---|---|---|---|---|---|---|---|---|
| (L-2-amino-4-methylphosphino-butyryl)-L-alanyl-L-alanine mono-diethanolammonium salt | 0.05 | +++ | +++ | ++++++ | +++ | +++ | +++ | |
| | 0.1 | + | + | + | ++ | ++ | ++ | ++ |
| | 0.2 | − | − | − | − | − | − | − |
| L-AMPB choline | 0.05 | + | − | ± | ± | − | − | − |
| | 0.1 | − | − | − | − | − | − | − |
| | 0.2 | − | − | − | − | − | − | − |
| DL-AMPB choline | 0.05 | +++ | + | ++ | ++ | ++ | ++ | ++ |
| | 0.1 | ++ | ± | + | − | − | − | − |
| | 0.2 | + | − | − | − | − | − | − |
| SF-1293 choline | 0.05 | ++ | ++ | ++ | ++ | ++ | ++ | ++ |
| | 0.1 | − | − | ± | − | − | − | − |
| | 0.2 | − | − | − | − | − | − | − |
| Glyphosate | 0.05 | +++ | +++ | ++++++ | +++ | +++ | +++ | |
| | 0.1 | +++ | +++ | ++++++ | +++ | +++ | +++ | |
| | 0.2 | ++ | ++ | ++++++ | ++ | +++ | +++ | |
| 2,2,3,3-Tetrafluoro propionic acid sodium salt | 0.1 | +++ | +++ | ++++++ | +++ | +++ | +++ | |
| | 0.2 | +++ | +++ | ++++++ | +++ | +++ | +++ | |
| | 0.4 | +++ | +++ | ++++++ | +++ | +++ | +++ | |
| None | 0 | +++ | +++ | ++++++ | +++ | +++ | +++ | |

Remarks:
O: Japanese bush cranberry (*Viburnum dilatatum* Thunb.)
P: kiichigo (*Rubus palmatsu* Thunb. forma *coptophyllus* Makino)
Q: Japanese prickly ash (*Xanthoxylum piperitum* DC.)
R: lace shrub (*Stephanandra incisa* Zabel)
S: yamazakura (*Prunus donarium* Sieb. var. *spontanae* Makino)
T: torch azalea (*Rhododendoron Kaempferi* Planch.)
U: oak (*Quercus serrata* Thunb)

EXPERIMENT 4

Water was placed in 20 cm.×30 cm. plastic vessels and a liquid fertilizer was added thereto.

Two water hyacinths were floated in each vessel. 0.1 or 0.2% of each of surfactants listed in Table 6 were added to 0.1 or 0.2% aqueous solutions of DL-AMPB choline. Each solution was sprayed by foliar application in an amount of 100 liter per 10 are. The killing index (0, no effect; 5, death) after 21 days and 3 months and the reproduction-inhibiting effect (−, no reproduction; +++, maximum reproduction) after 3 months were determined. The result are shown in Table 6.

TABLE 6

| Surfactant and the concentration (%) | | DL-AMPB choline concentration (%) | | | |
|---|---|---|---|---|---|
| | | After 21 days | | After 3 months | |
| | | 0.1 | 0.2 | 0.1 | 0.2 |
| Polyoxyethylene sorbitan monostearate | 0.1 | 2.5 | 4.5 | 2 ++ | 5 − |
| | 0.2 | 3 | 5 | 4 ± | 5 − |
| Polyoxyethylene sorbitan monooleate | 0.1 | 2.5 | 4.5 | 2 ++ | 5 − |
| | 0.2 | 3 | 5 | 4 ± | 5 − |
| Octylphenyl polyoxyethanol | 0.1 | 3 | 5 | 3 + | 5 − |
| | 0.2 | 3 | 5 | 4.5 ± | 5 − |
| Polyoxyethylene alkylaryl ether | 0.1 | 2.5 | 4.5 | 2 ++ | 5 − |
| | 0.2 | 3 | 5 | 4 ± | 5 − |
| Polyoxyethylene dodecyl ether | 0.1 | 2.5 | 4.5 | 2 ++ | 5 − |
| | 0.2 | 3 | 5 | 4 ± | 5 − |
| No surfactant | | 2 | 4 | 1 +++ | 4.5 ± |
| None | | 0 | | 0 +++ | |

EXPERIMENT 5

Water was placed in 20 cm.×30 cm. plastic vessels and a liquid fertilizer was added thereto. Two water hyacinths were floated in each vessel.

0.1 or 0.2% aqueous solutions of each of the compounds of the invention listed in Table 7 were sprayed by foliar application in an amount of 100 liter per 10 are. As a surfactant, 0.1% of octylphenyl polyoxyethanol was added.

The killing index (0, no effect; 5, death) after 21 days and 3 months, and the reproduction-inhibiting effect (−, no reproduction; +++, maximum reproduction) after 3 months were determined. The results are shown in Table 7.

TABLE 7

| | Concentration (%) | | | |
|---|---|---|---|---|
| | After 21 days | | After 3 months | |
| Compound | 0.1 | 0.2 | 0.1 | 0.2 |
| SF-1293 choline | 4 | 5 | 4 ± | 5 − |
| L-AMPB choline | 5 | 5 | 5 − | 5 − |
| DL-AMPB choline | 3 | 5 | 3 + | 5 − |
| SF-1293 monosodium salt | 3 | 4.5 | 3 + | 5 − |
| SF-1293 disodium salt | 3 | 4.5 | 3 + | 5 − |
| SF-1293 monopotassium salt | 3 | 4.5 | 3 + | 5 − |
| SF-1293 dipotassium salt | 3 | 4.5 | 3 + | 5 − |
| SF-1293 monodiethylammonium salt | 3 | 4.5 | 3 + | 5 − |
| SF-1293 monodiisopropylammonium salt | 3 | 4.5 | 3 + | 5 − |
| SF-1293 mono-n-butylammonium salt | 3 | 4.5 | 3 + | 5 − |
| SF-1293 diammonium salt | 3 | 4.5 | 3 + | 5 − |
| SF-1293 | 3 | 4.5 | 3 + | 5 − |
| L-AMPB monosodium salt | 4 | 5 | 4 ± | 5 − |
| L-AMPB disodium salt | 4 | 5 | 4 ± | 5 − |
| L-AMPB monopotassium salt | 4 | 5 | 4 ± | 5 − |
| L-AMPB dipotassium salt | 4 | 5 | 4 ± | 5 − |
| L-AMPB monodiethylammonium salt | 4 | 5 | 4 ± | 5 − |
| L-AMPB monoisopropylammonium salt | 4 | 5 | 4 ± | 5 − |
| L-AMPB mono-n-butylammonium salt | 4 | 5 | 4 ± | 5 − |
| L-AMPB diammonium salt | 4 | 5 | 4 ± | 5 − |
| L-AMPB | 4 | 5 | 4 ± | 5 − |
| DL-AMPB monosodium salt | 2 | 4 | 2 ++ | 4 ± |
| DL-AMPB disodium salt | 2 | 4 | 2 ++ | 4 ± |
| DL-AMPB monopotassium salt | 2 | 4 | 2 ++ | 4 ± |
| DL-AMPB dipotassium salt | 2 | 4 | 2 ++ | 4 ± |
| DL-AMPB monodiethylammonium salt | 2 | 4 | 2 ++ | 4 ± |
| DL-AMPB monoisopropylammonium salt | 2 | 4 | 2 ++ | 4 ± |
| DL-AMPB mono-n-butylammonium salt | 2 | 4 | 2 ++ | 4 ± |
| DL-AMPB diammonium salt | 2 | 4 | 2 ++ | 4 ± |

TABLE 7-continued

| Compound | Concentration (%) | | | |
|---|---|---|---|---|
| | After 21 days | | After 3 months | |
| | 0.1 | 0.2 | 0.1 | 0.2 |
| DL-AMPB | 2 | 4 | 2 ++ | 4 ± |
| None | 0 | | 0 +++ | |

EXPERIMENT 6

A paddy field soil was packed in 50 cm. square concrete pots. omodaka (*Sagittaria trifolia* L.), urikawa (*Sagittaria pygmaea* Miq.), prog-bit (*Hydrocharis dubia*) and aginashi (*Sagittaria Aginashi* Makino) were transplanted; then water was poured onto the soil at 5 cm. depth.

Further, water hyacinth, greater-duckweed (*Spirodela polyrhiza* Schleid.) and duckweed (*Lemna paucicostata* Hegelm) were floated on the water.

After one month, the compounds of the invention diluted to the prescribed concentrations as indicated in Table 8 were sprayed in an amount of 100 liter per 10 are. As a surfactant, 0.1% of octylphenyl polyoxyethanol was added thereto.

The killing index (0, no effect; 5, death) after 21 days and 3 months and the reproduction-inhibiting effect (−, no reproduction; +++, maximum reproduction) after 3 months were determined.

The results are shown in Table 8.

TABLE 8

| Compound and the concentration (%) | | After 21 days | | | | | | | After 3 months | | | | | |
|---|---|---|---|---|---|---|---|---|---|---|---|---|---|---|
| | | V | W | X | Y | Z | A' | B' | V | W | X | Y | Z | A' | B' |
| DL-AMPB choline | 0.05 | 3 | 2 | 2 | 2 | 1 | 3 | 3 | 2++ | 2++ | 2++ | 2++ | 1+++ | 3+ | 3+ |
| | 0.1 | 4 | 3 | 3 | 3 | 3 | 4 | 4 | 4± | 3+ | 4± | 4± | 3++ | 5− | 5− |
| | 0.2 | 4.5 | 4 | 4 | 4 | 5 | 5 | 5 | 5− | 5− | 5− | 5− | 5− | 5− | 5− |
| L-AMPB choline | 0.05 | 3 | 3 | 3 | 3 | 3 | 4 | 4 | 4+ | 3+ | 4+ | 4± | 3++ | 5− | 5− |
| | 0.1 | 4.5 | 4 | 4 | 4 | 5 | 5 | 5 | 5− | 5− | 5− | 5− | 5− | 5− | 5− |
| | 0.2 | 5 | 5 | 5 | 5 | 5 | 5 | 5 | 5− | 5− | 5− | 5− | 5− | 5− | 5− |
| SF-1293 choline | 0.05 | 3 | 3 | 3 | 3 | 3 | 4 | 4 | 2++ | 2++ | 2++ | 2++ | 3++ | 3+ | 3+ |
| | 0.1 | 4 | 4 | 4 | 4 | 4.5 | 4.5 | 4.5 | 4± | 4± | 4± | 4± | 5− | 5− | 5− |
| | 0.2 | 5 | 5 | 5 | 5 | 5 | 5 | 5 | 5− | 5− | 5− | 5− | 5− | 5− | 5− |
| None | 0 | 0 | 0 | 0 | 0 | 0 | 0 | 0 | 0+++ | 0+++ | 0+++ | 0+++ | 0+++ | 0+++ | 0+++ |

Remarks:
V: omodaka (*Sagittaria trifolia* L.)
W: urikawa (*Sagittaria pygmaea* Miguel)
X: prog-bit (*Hydrocharis dubia*)
Y: aginashi (*Sagittaria Aginashi* Makino)
Z: water hyacinth (*Eichhornia crassipes* Solms)
A': greater-duckweed (*Spirodela polyrhiza* Sohleid.)
B': duckweed (*Lemna paucicostata* Hegelm)

EXPERIMENT 7

A black soil was packed in 50 cm. square concrete pots and water was poured there-onto at 50 cm. in depth. Hornwort (*Ceratophyllum demersum* L.), stonewort (*Chara Braunii* Gmel.) and salvinia (*Salvinia natans* All.) were transplanted and pond scum (*Spirogira crassa* Kütz) and diatoms (Bacillariophyta) were floated in the water.

Then, the compounds of the invention were applied dropwise onto the surface of the water so that the prescribed concentrations in the water are obtained as indicated in Table 9.

The controlling effect (0, no effect; 5, perfect control) after 21 days and 3 months was determined and the results are shown in Table 9.

TABLE 9

| Compound and the concentration (ppm) | | After 21 days | | | | | After 3 months | | | | |
|---|---|---|---|---|---|---|---|---|---|---|---|
| | | C' | D' | E' | F' | G' | C' | D' | E' | F' | G' |
| DL-AMPB choline | 1 | 2 | 3 | 3 | 2 | 3 | 1 | 1 | 2 | 1 | 1 |
| | 3 | 4.5 | 4.5 | 4 | 4 | 4 | 5 | 5 | 5 | 5 | 5 |
| | 10 | 5 | 5 | 5 | 5 | 5 | 5 | 5 | 5 | 5 | 5 |
| L-AMPB choline | 1 | 3 | 4 | 4 | 4 | 4 | 2 | 5 | 5 | 4 | 4 |
| | 3 | 5 | 5 | 5 | 5 | 5 | 5 | 5 | 5 | 5 | 5 |
| | 10 | 5 | 5 | 5 | 5 | 5 | 5 | 5 | 5 | 5 | 5 |
| SF-1293 choline | 1 | 2 | 3 | 3.5 | 2 | 2 | 1 | 2 | 3 | 1 | 1 |
| | 3 | 4 | 4 | 4.5 | 3.5 | 3 | 5 | 5 | 5 | 5 | 5 |
| | 10 | 5 | 5 | 5 | 5 | 5 | 5 | 5 | 5 | 5 | 5 |
| None | 0 | 0 | 0 | 0 | 0 | 0 | 0 | 0 | 0 | 0 | 0 |

Remarks:
C': hornwort (*Ceratophyllum demersum* L.)
D': stonewort (*Chara Braunii* Gmel.)
E': salvinia (*Salvinia natans* Allioni)
F': pond scum (*Spirogira crassa* Kutz.)
G': diatoms (Bacillariophyta)

We claim:

1. A compound of formula (I) or (II):

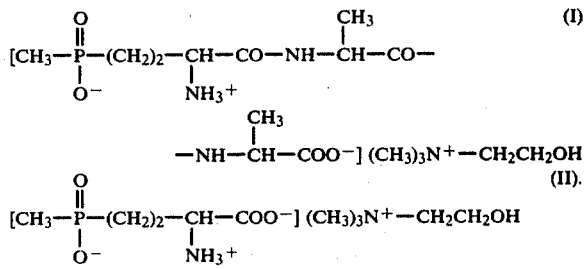

2. A herbicidal composition for controlling weeds, shrubs and aquatic plants which comprises an effective amount of a compound as claimed in claim 1 and an agriculturally acceptable carrier.

3. A method of destroying weeds, shrubs and aquatic plants which comprises applying thereto an effective amount of a compound as claimed in claim 1.

4. The herbicidal composition of claim 2, wherein said compound is (2-amino-4-methylphosphinobutyryl-)alanylalanine choline.

5. The herbicidal composition of claim 2, wherein said compound is 2-amino-4-methylphosphinobutanoic acid choline.

6. The herbicidal composition of claim 2, wherein said compound is DL-2-amino-4-methylphosphinobutanoic acid choline.

7. The herbicidal composition of claim 2, wherein said compound is L-2-amino-4-methylphosphinobutanoic acid choline.

8. The method of claim 3, wherein said compound is (2-amino-4-methylphosphinobutyryl)alanylalanine choline.

9. The method of claim 3, wherein said compound is 2-amino-4-methylphosphinobutanoic acid choline.

10. The method of claim 3, wherein said compound is DL-2-amino-4-methylphosphinobutanoic acid choline.

11. The method of claim 3, wherein said compound is L-2-amino-4-methyl-phosphinobutanoic acid choline.

12. The method of claim 3, wherein an effective amount of said compound is applied for controlling weeds.

13. The method of claim 3, wherein an effective amount of said compound is applied for controlling shrubs.

14. The method of claim 3, wherein an effective amount of said compound is applied for controlling aquatic plants.

15. The method of claim 12, wherein said compound is DL-2-amino-4-methylphosphinobutanoic acid choline.

16. The method of claim 13, wherein said compound is DL-2-amino-4-methylphosphinobutanoic acid choline.

17. The method of claim 14, wherein said compound is DL-2-amino-4-methylphosphinobutanoic acid choline.

18. The method of claim 3, which comprises applying to the weeds, shrubs and aquatic plants an amount of a compound as claimed in claim 1 sufficient for the purpose of killing, and inhibiting reproduction of, said weeks, shrubs and aquatic plants.

19. The method of claim 18, wherein said compound is DL-2-amino-4-methylphosphinobutanoic acid choline.

20. The method of claim 18, wherein said compound is L-2-amino-4-methylphosphinobutanoic acid choline.

21. The compound of claim 1, wherein said compound has the formula I.

22. The compound of claim 1, wherein said compound has the formula II.

* * * * *

UNITED STATES PATENT AND TRADEMARK OFFICE
CERTIFICATE OF CORRECTION

PATENT NO. : 4,226,610
DATED : October 7, 1980
INVENTOR(S) : TETSUO TAKEMATSU et al It is certified that error appears in the above—identified patent and that said Letters Patent is hereby corrected as shown below:

Column 4, line 23: after "Castanea crenata Sieb", replace "or" with ---et---.

Columns 15-16, Table 5, first column, sixth compound:

replace "(L-2-Amino-4-butyryl) . . ." with

---(L-2-Amino-4-methylphosphinobutyryl) . . .---.

Signed and Sealed this

Thirteenth Day of January 1981

[SEAL]

Attest:

SIDNEY A. DIAMOND

Attesting Officer

Commissioner of Patents and Trademarks

UNITED STATES PATENT AND TRADEMARK OFFICE
CERTIFICATE OF CORRECTION

PATENT NO. : 4,226,610
DATED : October 7, 1980
INVENTOR(S) : TETSUO TAKEMATSU et al It is certified that error appears in the above—identified patent and that said Letters Patent is hereby corrected as shown below:

Column 1, line 40, before "L-Form" insert --The compound referred to as AMPB which is named herein 2-amino-4-methylphosphinobutanoic acid is by the latest nomenclature named 2-amino-4-(hydroxy)(methyl)phosphinoylbutyric acid in accordance with the International Union of Pure And Applied Chemistry, "Nomenclature Of Organic Chemistry", pages 384, 385 and 403 (1979 Edition).--.

Signed and Sealed this

Fourth Day of May 1982

[SEAL]

Attest:

GERALD J. MOSSINGHOFF

Attesting Officer    Commissioner of Patents and Trademarks